United States Patent [19]

Weikel

[11] 4,349,125
[45] Sep. 14, 1982

[54] SLIDING DENTAL AMALGAM DISPENSER

[76] Inventor: Maurice M. Weikel, Las Vegas, Nev.

[21] Appl. No.: 221,807

[22] Filed: Dec. 31, 1980

Related U.S. Application Data

[63] Continuation-in-part of Ser. No. 190,627, Sep. 25, 1980, which is a continuation-in-part of Ser. No. 951,079, Oct. 13, 1978, abandoned.

[51] Int. Cl.³ .................... G01F 11/22; G01F 11/24; A47F 1/035; B65D 83/04
[52] U.S. Cl. ..................... 221/96; 222/307; 222/361; 222/325; 222/324; 222/188; 222/478
[58] Field of Search ............... 221/96; 222/305, 306, 222/307, 308, 370, 325, 323, 324, 361, 188, 478

[56] References Cited

U.S. PATENT DOCUMENTS

| | | | |
|---|---|---|---|
| 1,462,954 | 7/1923 | Burnett | 222/308 X |
| 1,767,928 | 6/1930 | Jellison | 222/380 X |
| 2,844,284 | 7/1958 | Ackerman, Jr. | 222/306 X |
| 3,040,934 | 6/1962 | Weiner | 222/308 X |
| 3,128,907 | 4/1964 | Weiner | 222/307 X |
| 3,168,213 | 2/1965 | De Gon | 221/96 |
| 3,521,793 | 7/1970 | McShinley | 222/308 X |
| 4,139,030 | 2/1979 | Schroeder | 221/96 X |

*Primary Examiner*—Allen N. Knowles
*Attorney, Agent, or Firm*—Fulwider, Patton, Rieber, Lee & Utecht

[57] ABSTRACT

A trigger-actuated sliding dental amalgam dispenser is provided with a material distribution shell within which a transport carriage is longitudinally reciprocated under the control of a trigger actuator. Liquid conduit channels in the shell carry mercury from a reservoir above the shell to a measuring chamber in the carriage. Upon actuation of the trigger, the measuring chamber, otherwise held in communication with the mercury reservoir by a spring bias on the trigger, is reciprocated relative to the shell to that the mercury in the measuring chamber is discharged into a dispensing well. Concurrently, a slide with a silver receptacle tray is repositioned to receive another tablet of silver from a tablet dispensing cartridge positioned above the material distribution shell. When the trigger is released, the tray carries the silver tablet into vertical registration with the dispensing well to drop the tablet into the well. A micropore filter communicates with the measuring chamber through a relief vent when the measuring chamber is in communication with the mercury reservoir to allow air to escape as mercury fills the volume of the measuring chamber, while at the same time preventing the escape of mercury therethrough. A vacuum break vent is preferably located to communicate with the measuring chamber when the chamber is moved into registration with the dispensing well.

19 Claims, 6 Drawing Figures

SLIDING DENTAL AMALGAM DISPENSER

BACKGROUND OF THE INVENTION

This application is a continuation-in-part of U.S. patent application Ser. No. 190,627 entitled ROTARY DENTAL AMALGAM DISPENSER, filed on Sept. 25, 1980 in the U.S. Patent and Trademark Office, which is a continuation-in-part of U.S. application Ser. No. 951,079, filed Oct. 13, 1978, now abandoned.

FIELD OF THE INVENTION

The present invention relates to devices for dispensing mercury and silver for mixture into a dental amalgam.

DESCRIPTION OF THE PRIOR ART

Various devices have been utilized to effectuate the dispensation of aliquot quantities of mercury and silver for mixture to form a dental amalgam. The amalgam forms a soft, pliable paste when the silver and mercury are initially mixed, but quickly and permanently hardens to form a permanent filling for a tooth.

Various prior art devices employed for dispensing the amalgam components have employed a reciprocal slide in which manual force is axially exerted directly along the line of movement of the slide within a housing. Typically, the application of force is exerted by the pressure of the thumb of the user. Although conventional reciprocal mechanisms employ guide components to produce proper alignment, the conventional reciprocating mechanisms are subject to considerable wear because of undesirable torsional forces which are applied to them and because of the high degree of physical wear which occurs. In this connection, conventional reciprocating mechanisms typically employ reciprocal steel guides which wear against the structure of a plastic housing. As a result, mercury leakage occurs and imprecise quantities of mercury are dispensed.

SUMMARY OF THE INVENTION

The present invention involves the use of a sliding transport carriage that operates within a linear track or groove in a material distribution shell for reciprocal movement therealong. The relative movement between the distribution shell and the carriage is controlled by a handle which is connected to the shell and a trigger which is connected to the carriage at a sliding connection and to the shell at a fulcrum displaced from the sliding connection. Alternatively, the connections of the handle and trigger to the shell and carriage can be reversed. A spring mechanism normally biases the handle and trigger apart, so that squeezing the handle and the trigger together brings the measuring chamber from communication with the mercury reservoir to communication with a dispensing well in the material distribution shell. Also, a tablet tray is moved with the transport carriage to receive tablets of silver, one by one, each time the handle and trigger are squeezed together, and to dispense those tablets into the dispensing well when the handle and trigger are released.

Within the material distribution shell a channel leads from the mercury reservoir to an inlet port interface in the wall of the track within which the transport carriage moves. Preferably, the channel from the mercury reservoir to the inlet port is constructed with a vertical duct extending downwardly therefrom and an inclined duct extending upwardly toward the wall of the track.

The measuring chamber itself is defined in the transport carriage as an inclined bore with its lower extremity at the level of the inlet port. In a wall of the track on the opposite side of the transport carriage from the inclined duct there is a relief vent located at the level of the upper end of the measuring chamber. The relief vent leads to a cavity in the material distribution shell in which a micropore filter is located.

The mercury reservoir is located above the level of the measuring chamber so that the existence of a head of mercury forces mercury from the lower extremity of the vertical duct beneath the reservoir up the inclined duct of the channel and into the measuring chamber when the trigger is biased apart from the handle by the spring mechanism. The measuring chamber fills completely, since displaced air is forced out of the dental amalgam dispenser through the relief vent and thence through the micropore filter. The micropore filter will not, however, allow mercury to escape.

An outlet port is longitudinally displaced from the inlet port in a wall of the track in the material distribution shell. The outlet port is located at a level no higher than the inlet port, and at a level in registration with the lowermost portion of the measuring chamber. The outlet port leads to a downwardly inclined channel which empties into a dispensing well. A vacuum break vent is defined in structure in the material distribution shell for communication with the measuring chamber when the transport carriage is reciprocally moved to align the measuring chamber with the outlet port. This ensures that all of the mercury empties from the measuring chamber into the dispensing well, and that a vacuum does not form which might retain mercury in the measuring chamber.

The dental amalgam dispenser is preferably adapted to receive a tablet dispensing cartridge having a plurality of parallel, equally spaced vertical tubes for holding columnar stacks of tablets of silver. A desired tube may be positioned in a track directly above the aperture in the shell, so that tablets of silver may be dispensed from the selected tube, one at a time. When all of the tablets have been dispensed from one tube, the cartridge is advanced incrementally along the track to bring another tube into alignment with the aperture.

It is an object of the present invention to provide a dental amalgam dispenser with a spring-loaded trigger mechanism that can be operated to effectuate reciprocal motion of a transport carriage to discharge aliquot quantities of mercury and silver for mixture into an amalgam. In this connection, it is a further object to avoid the undesirable wear attributable to the application of unwanted torque in a conventional reciprocal dental amalgam dispensing device. Manual force to reciprocate the carriage within the track is applied at a sliding connection which avoids the application of torsional forces to the transport carriage. The sliding connection is preferably formed by a slot in the trigger transverse to the direction of movement of the transport carriage, and a bearing post secured to the carriage and extending outwardly through the slot. The forces applied linearly along the path of movement of the transport carriage are therefore free from undesirable torsional components, since the bearing post slides freely within the slot in the trigger.

Preferably, the volume of the measuring chamber in the transport carriage is adjustable. Adjustment is performed by means of a metering rod. The rod is longitudinally adjustable in an attitude of advancement toward or withdrawal from the measuring chamber. This decreases or increases the volume of the chamber, and hence decreases or increases the volume of the mercury transported within the chamber from the inlet port to the outlet port. Because of the avoidance of torsional forces, the tolerances between the width of the transport carriage and the width of the track or channel within which the transport carriage moves can be quite close. Moreover, both the material distribution shell and the transport carriage can be constructed of the same material, preferably lucite plastic, so as to minimize frictional wear. Nevertheless, a secure, leak-proof seal exists between the outer walls of the transport carriage and the inner walls of the material distribution shell.

The invention may be described with greater clarity and particularity by reference to the accompanying drawings.

DESCRIPTION OF THE PREFERRED EMBODIMENT

Figure 1:
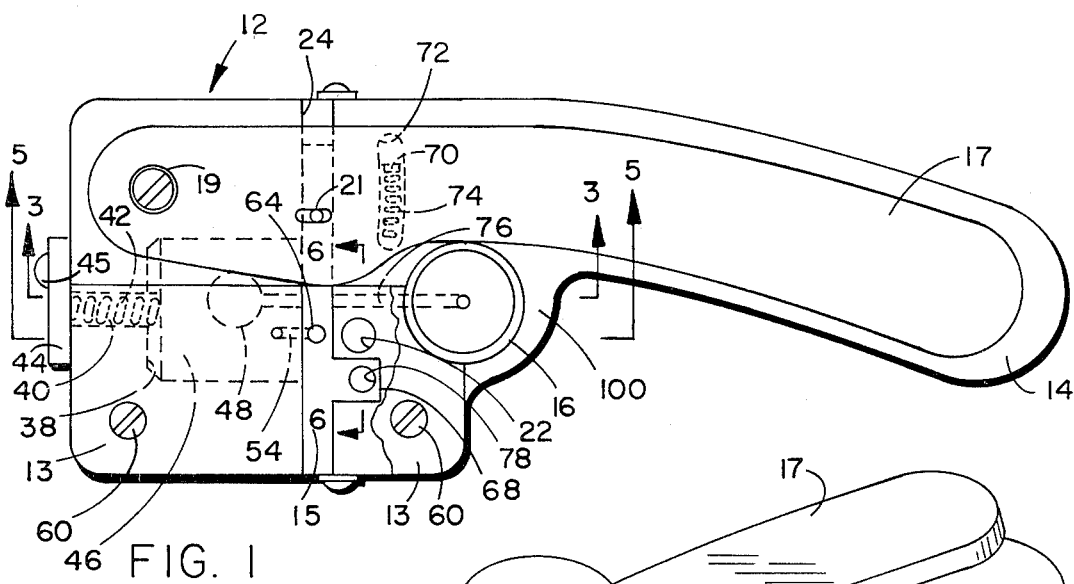
FIG. 1 is a top plan view of a dental amalgam dispenser according to the invention showing actuation of the trigger thereof.
Figure 2:
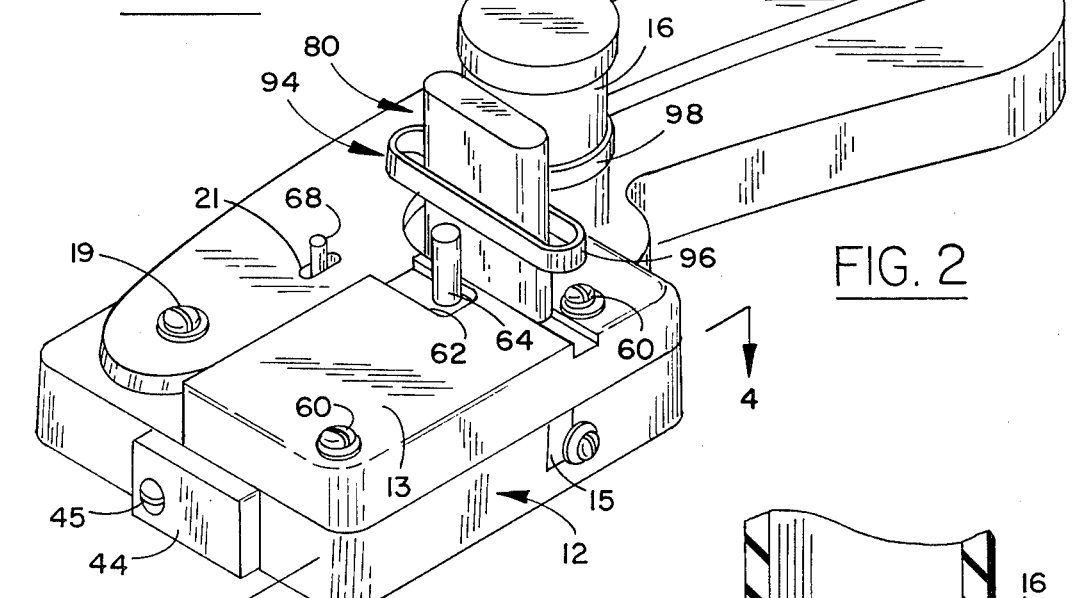
FIG. 2 is a perspective view of the embodiment of FIG. 1 showing the trigger released.
Figure 4:
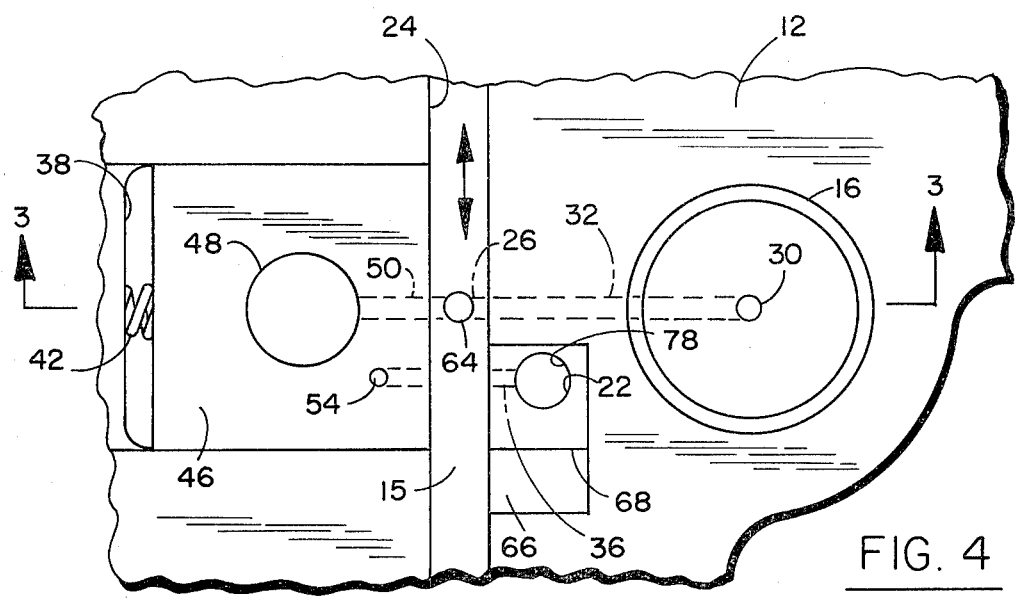
FIG. 4 is a sectional elevational view of a portion of the dispenser taken along the lines 4—4 of FIG. 2.
Figure 5:
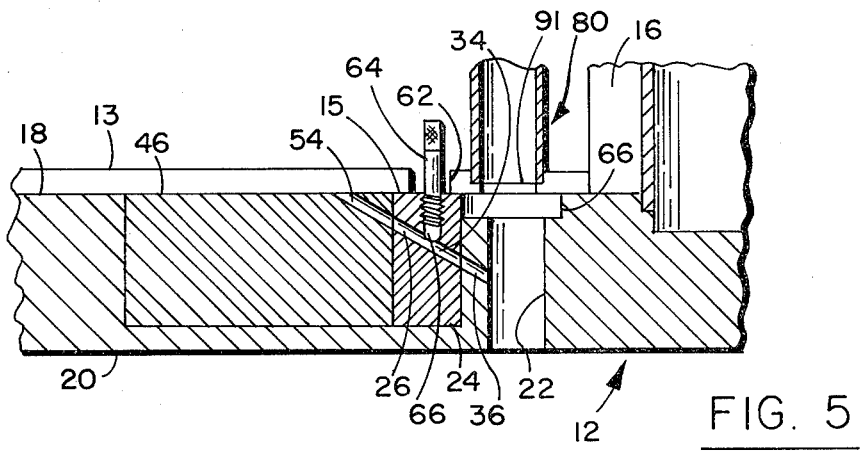
FIG. 5 is a sectional elevational view of the dispenser taken along the lines 5—5 of FIG. 1.

A dental amalgam dispenser 10, illustrated in FIGS. 1 and 2, includes a generally rectangular shaped molded lucite material distribution shell 12 with a unitary elongated handle 14. The material distribution shell 12 is constructed to receive a cylindrical mercury distribution reservoir 16 in a shallow recess in the manner depicted in FIG. 3. As illustrated in FIG. 5, the material distribution shell 12 is defined with an upper surface 18 and a lower surface 20 between which a vertical dispensing well 22 is defined. A linear track 24 of rectangular cross-section, is laterally displaced from the dispensing well 22, as illustrated in FIGS. 1, 4 and 5.

Figure 3:
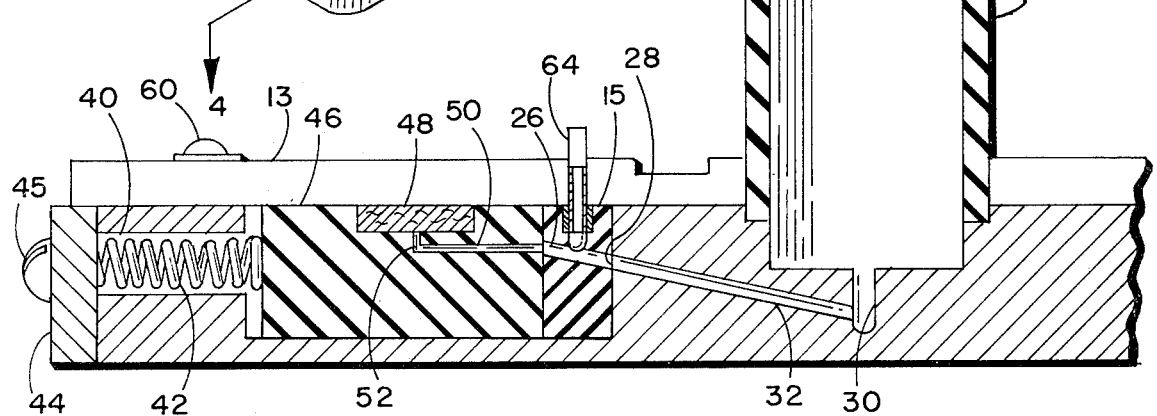
FIG. 3 is a sectional elevational view of the dispenser of FIG. 1 taken along the lines 3—3 of FIG. 1.

A flat rectangular mounting deck 13 is partially broken away in FIG. 1 to allow illustration of an elongated, molded lucite bar-shaped transport carrier 15, visible in cross section in FIGS. 3 and 5. The transport carriage 15 is longitudinally reciprocal along the linear track 24 in the material distribution shell 12 under the control of a trigger 17 which is fastened to the material distribution shell 12 at a rotatable fulcrum connection 19, illustrated in FIGS. 1 and 2. The trigger 17 is fastened to the transport carriage 15 at a sliding connection which is displaced from the fulcrum 19. The transport carriage 15 carries a measuring chamber 26 between the position depicted in FIG. 3, where it is filled with mercury, to the position depicted in FIG. 5, at which mercury is discharged into the dispensing well 22. A micropore filter 48, illustrated in FIGS. 3 and 4 ensures that the measuring chamber 26 is completely filled, while a vacuum break 54 depicted in FIGS. 4 and 5, assures complete discharge of the mercury from the measuring chamber 26.

A channel is defined within the material transport shell 12 to conduct mercury from the reservoir 16 to a measuring chamber 26 defined within the transport carriage 15, as illustrated in FIG. 3. The channel leads from an inlet port 28 defined in one of the vertical walls of the track 24 and is formed by a vertical duct 30 descending from the mercury reservoir 16, and an inclined duct 32 that intersects both the vertical duct 30 and the transfer inlet 28.

As depicted in FIG. 5, a transfer outlet port 34 is defined in the wall of the track 24 longitudinally displaced from the inlet port 28 and located at a level no higher than the inlet port 28. From the outlet port 34 an inclined duct 36 leads downwardly to intersect with the dispensing well 22.

Figure 6:
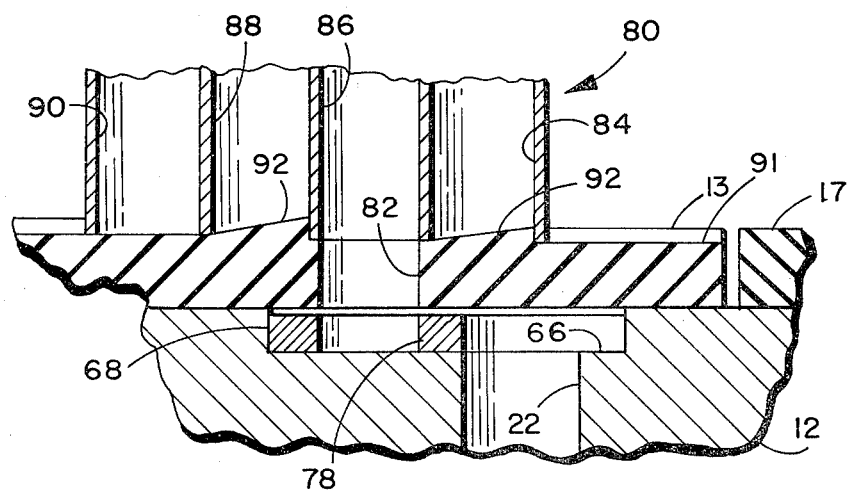
FIG. 6 is a sectional detail taken along the lines 6—6 of FIG. 1.

In the top surface of the material distribution shell 12 an elongated recess 66 extending parallel to the track 24 is defined to receive a flat tablet tray 68 that extends as an ear laterally outward from the carriage 15, as illustrated in FIGS. 4-6. The tray 68 moves with the carriage 15 in reciprocal fashion within the recess 66.

The material distribution shell 12 is formed with a transverse generally rectangular shaped cavity 38 therein, as illustrated in FIG. 4. The cavity is bounded on one side by the track 24, thereby defining a gap therein, and a bore 40, illustrated in FIGS. 1 and 3, is defined through the structure of the material distribution shell 12 to intersect the cavity 38. A coil spring 42 is disposed within the bore 40, and is held in a compressed state by a lucite retaining tab 44 that is secured by a screw 45 which is threaded into the structure of the material distribution shell 12. A flat, rectangular slab 46 is disposed within the cavity 38 and is biased inwardly toward the track 24 by the compressed spring 42 which bears thereagainst. The force of the spring 42 is chosen so as to effectuate a leakproof seal between the material transport carriage 15 and the slab 46 on the one side and between the material transport carriage 15 and the wall of the track 24 in the material distribution shell 12 on the other. Another factor in the choice of the spring 42 is the necessity for the force thereof not to be so great as to create excessive friction which might prevent movement of the transport carriage 15 under control of the trigger 17.

A shallow, vertical well is defined within the structure of the slab 46 and a disc shaped micropore filter 48 is positioned therewithin, as depicted in FIGS. 3 and 4. A relief vent is defined within the slab 46 as a horizontal bore 50 that extends from the face of the slab 46 that resides in sliding contact with the carriage 15 to a short vertical duct 52 that extends downwardly from the well within which the micropore filter 48 resides.

As illustrated in FIG. 5, an inclined bore 54 is also defined in the slab 46 to extend from the flat top surface thereof downwardly and at an angle so as to also intersect the wall of the slab 46 which resides in sliding contact with the transport carriage 15. The bore 54 is in linear alignment with the outlet duct 36 defined in the material distribution shell 12, as depicted in FIGS. 4 and 5.

The measuring chamber 26 within the bar shaped transport carriage 15 is defined as an inclined bore therethrough. The lower extremity of the measuring chamber 26 is at the same vertical level as the inlet port 28 and the outlet port 34 in the material distribution shell 12. The upper extremity of the measuring chamber 26 is on the opposite side thereof and resides at the level of the opening of the lateral bore 50 of the relief vent and at the level of the opening of the vacuum break bore 54 in the vertical side of the slab 46.

The rectangular mounting deck 13 is secured atop a portion of the material distribution shell 12 by means of machine screws 60. At the edge of the mounting deck 58 facing the trigger 17, there is a recess 62 extending parallel to and above the linear track 24. The recess 62 is adapted to receive an upwardly extending metering rod 64, the lower extremity of which is threadably engaged in the structure of the transport carriage 15, and the tip 66 of which extends into the measuring chamber 26. The metering rod 64 protrudes into the inclined bore forming the measuring chamber 26 to an adjustable degree, thereby providing means for altering the volume of the measuring chamber 26. To increase the volume, the metering rod 64 is rotated counterclockwise, so as to withdraw the tip 66 from extended protrusion into the measuring chamber 26. To reduce the volume, the metering rod 64 is rotated in the opposite direction. The recess 62 accommodates the longitudinal movement of the metering rod 64 with the carriage 15.

The trigger 17 is an elongated structure which is rotatably secured to the material distribution block 12 at the fulcrum screw connection 19. A slot 21 is defined completely through the trigger 17 and extends transverse to the direction of alignment of the transport carriage 15 directly thereabove. A bearing post 69 extends vertically upwardly from the material transport shell 15 through the slot 21. Rotation of the lever arm of the trigger 17 about the fulcrum 19 causes the walls of the slot 21 to act against the bearing post 69 to reciprocate the carriage transport 15 longitudinally along the track 24. No torsional component of force is exerted on the bearing post 69, since the slot 21 is long enough to prevent such a force from being exerted.

From the underside of the trigger 17, there is a downwardly depending finger 70 which projects into an arcuate cavity 72 defined in the material distribution shell 12, as illustrated in FIG. 1. The center of the radius of curvature of the arcuate cavity 72 is at the fulcrum connection 19. A coil spring 74 is maintained in compression in the cavity 72 to bear against the finger 70 and the end of the cavity 72. This biases the trigger 17 in a counterclockwise direction relative to the material distribution shell 12, as viewed in FIG. 1.

The tray or slide 68 extends laterally from the upper portion of the transport carriage 15 into the recess 66 on the top surface of the material distribution shell 12, as illustrated in FIGS. 1, 4 and 6. The tray 68 has defined therein an aperture 78. The aperture 78 in the tray 68 receives the tablets of silver from a cartridge 80 through a bore 82 in the mounting plate 13. The tray 68 receives the tablets of silver, one at a time, when the trigger 17 is squeezed relative to the handle 14 as depicted in FIG. 1. In the position of FIG. 1 the aperature 78 of the tray 68 is in vertical registration with the bore 82, which is illustrated in elevational section in FIG. 6. When released, the spring 74 returns the trigger 17 from the position of FIG. 1 to the position depicted in FIG. 2, thereby carrying the entrapped tablet of silver from the bore 82, illustrated in FIG. 6 to the dispensing well 22 in the material distribution block 12, as illustrated in FIG. 4.

The tablet dispensing cartridge 80, is an oblong, thin, upright plastic structure into which a plurality of parallel, equally spaced vertical tubes 84, 86, 88, 90 of equal diameter are defined for holding columnar stacks of disk-like tablets of silver, as illustrated in FIG. 6. The cartridge 80 is moveable along a longitudinal track or groove 91 defined in the upper surface of the mounting deck 13 to align a selected one of the tubes 84-90 with the aperture 82 in the mounting deck 13 to dispense tablets from the selected tube through the aperture 82 and into the tray 68.

In the channel of the groove 91 there are a pair of positioning lugs 92 on either side of the bore 82. Each lug 92 is a short pedestal configured to project upwardly from the groove 91 and to slope upwardly and toward the trigger 17. The positioning lugs 92 each fit into one of the tubes 84-90 or into abutment with the wall at one of the ends of the cartridge 80. The engagement of a project lug 92 in an appropriate one of the tubes, or against the end of the cartridge 80, can be sensed by the user as the user moves the cartridge 80 along the groove 91 so that proper vertical alignment of a selected one of the tubes 84-90 can be assured.

As illustrated in FIG. 2, the dentral amalgam dispenser 10 may be provided with a retaining bracket 94. The retaining bracket 94 and the cartridge 80 are omitted from FIG. 1 for clarity of illustration of other portions of the dispenser 10. The retaining bracket 94 is configured with an oblong, elongated band 96 to receive the cartridge 80 for longitudinal reciprocation therewithin. Attached to the band 96 is a mounting ring 98 which is of cylindrical annular configuration and is secured about the structure of the reservoir 16 by means of a locking screw and nut assembly. When the locking assembly is tightened, the retaining bracket 98 is secured relative to the material distribution shell 12 above the mounting deck 13. The cartridge 80 can thereby be adjustably positioned along the groove 91 to align the selected tube 84-90 with aperture 82 in the mounting deck 13 in the manner previously described. With the retaining bracket 94, the dental amalgam dispenser 10 can be moved freely about and the cartridge 80 will not fall out but will remain in position on the mounting deck at 13.

In the operation of the dental amalgam dispenser 10, the cartridge 80 is first positioned in the groove 91 and held within the confines of the retaining loop 96 of the retaining bracket 94. The cartridge 80 is longitudinally adjusted, using the positioning lugs 92 in the manner described in connection with FIG. 6. The trigger 17 is then squeezed toward the handle 14, as illustrated in FIG. 1. Sufficient force is required to compress the spring 74, depicted in FIG. 1, which otherwise biases the trigger 17 and handle 14 apart.

Until the trigger 17 and handle 14 are compressed, mercury flows from the reservoir 16 down through the vertical duct 30 and up the inclined duct 32, through the inlet port 28, and into the inclined measuring chamber 26, all illustrated in FIG. 3. Mercury will not pass through the micropore filter 48, but air displaced from the ducts 30 and 32 and the measuring chamber 26 is exhausted through the bores 50 and 52 and through the micropore filter 48. The head of mercury in the reservoir 16 is sufficient to force the mercury up the inclined duct 32 and the inclined measuring chamber 26. As previously noted, the metering rod 64 can be used to alter the amount of mercury in the measuring chamber 26.

When the trigger 17 and handle 14 are squeezed together, the structure of the trigger 17 bears against the bearing post 69 at the slot 21 in the trigger structure. The transport carriage 15 is thereby carried longitudinally along the slot 24 from the position depicted in FIGS. 2, 3 and 4 to the position depicted in FIGS. 1 and 5. In the position of FIG. 5, the lower extremity of the measuring chamber 26 is brought into communication with the outlet port 34, as illustrated in FIG. 5. Mercury thereupon flows out of the outlet port 34, through the channel 36 and into the dispensing well 22 to a container located thereabeneath. The vacuum break vent 54 allows air to follow the mercury and enter the measuring chamber 26 so that droplets of mercury are not held back by a vacuum, as might otherwise occur. Accordingly, the entire aliquot of mercury is discharged into the dispensing well 22.

As the trigger 17 and handle 14 are squeezed together, the aperture 78 in the tray 68 is brought into registration with the bore 82 in the groove 91 in the mounting deck 13, as illustrated in FIG. 6. The lowermost tablet is dispensed from the tube in the cartridge 80 located directly thereabove and into the aperture 78. When the trigger 17 is released, the spring 74 rotates the trigger 71 in an arcuate path counterclockwise, as viewed in FIG. 1, until the aperture 78 resides in vertical registration with the dispensing well 22. The tablet of silver discharged from the cartridge 80 into the tray 68 is thereby carried to the dispensing well 22.

While but a single embodiment of the invention has been depicted, it should be understood that numerous other variations and modifications of the invention will undoubtedly become readily apparent to those familiar with dental amalgam dispensers. For example, the track 24 need not be defined in the upper surface of the material transport shell 12, but rather could be a bore therethrough. Accordingly, the invention should not be considered as being limited to the specific embodiment depicted and described, but rather as defined in the claims appended hereto.

I claim:

1. A dental amalgam dispenser comprising:
    a mercury reservoir;
    a material distribution shell receiving said mercury reservoir and defining a dispensing well extending therethrough, a linear track laterally displaced from said dispensing well, a transfer inlet in said linear track, a channel for conducting mercury from said mercury reservoir to a transfer inlet in said linear track, a transfer outlet located in said linear track and longitudinally displaced from and vertically no higher than the level of said transfer inlet, and a channel for conducting mercury from said transfer outlet to said dispensing well;
    a transport carriage coupled to said shell for reciprocal movement along said track and including a tablet tray for carrying silver tablets to said dispensing well for discharge therein and wherein there is defined in said carriage a measuring chamber, and said carriage is reciprocal in sliding sealed engagement with said track to a position in which said measuring chamber is in communication with said transfer inlet and alternatively to a position in which said measuring chamber is in communication with said transfer outlet; and
    a handle connected to one of said shell and said carriage, and a trigger connected to the other thereof at a sliding connection and to said one thereof at a fulcrum, and spring means biasing said handle and trigger apart, whereby squeezing said handle and said trigger together brings said measuring chamber from communication with said transfer inlet to communication with said transfer outlet.

2. The dental amalgam dispenser of claim 1 wherein said sliding connection is formed by a slot in said trigger transverse to the direction of movement of said carriage, and a post secured to said carriage and extending outwardly through said slot.

3. The dental amalgam dispenser of claim 1 wherein said carriage is equipped with means for varying the volume of said measuring chamber.

4. The dental amalgam dispenser according to claim 1 further characterized in that said channel is defined in said material distribution shell to include a vertical duct descending from said mercury reservoir and an inclined duct intersecting both said vertical duct and said transfer inlet.

5. The dental amalgam dispenser according to claim 4 further comprising structure in sliding sealed engagement with said track in which a micropore filter is located, and a relief vent is defined in said structure to extend between said micropore filter and said transport carriage and in communication with said measuring chamber when said carriage is reciprocated to said position in which said measuring chamber is in communication with said transfer inelet.

6. The dental amalgam dispenser according to claim 5 further characterized in that a vacuum break vent is defined in said structure to communicate with said measuring chamber when said carriage is reciprocated to said position in which said measuring chamber is in communication with said transfer outlet.

7. The dental amalgam dispenser according to claim 5 further characterized in that said measuring chamber is defined in said transport carriage as an inclined bore sloping upwardly from said material distribution shell toward said relief vent.

8. The dental amalgam dispenser according to claim 7 further comprising a metering rod threadably engaged with said transport carriage for protrusion into said inclined bore to an adjustable extent, thereby providing means for altering the volume of said measuring chamber.

9. The dental amalgam dispenser according to claim 5 further characterized in that said material distribution shell is formed with a transverse cavity therein intersecting said track and said structure is a slab movably mounted within said transverse cavity, and with a spring biasing said slab toward said track.

10. A dental amalgam dispenser comprising:
    a material distribution shell having an upper surface and defining within said shell:
        (a) a dispensing well extending through said distribution shell from said upper surface to an outlet beneath;
        (b) a linear groove defined in said material distribution shell;
        (c) a channel from said upper surface to a transfer inlet in said groove;
        (d) a transfer outlet in said groove longitudinally displaced from said transfer inlet and no higher than the level thereof;
        (e) a downwardly inclined channel extending from said transfer outlet to said dispensing well;
    a transport carriage longitudinally reciprocal within said linear groove and in sliding sealing engagement with said material distribution shell and defining therewithin a measuring chamber in communication with said transfer inlet, the lower extremity of said measuring chamber being at the level of said transfer outlet;

a mercury reservoir extending above said upper surface of said shell and in communication with said channel leading to said transfer inlet; and, slide means coupled for movement with said carriage for receiving a measured quantity of silver from above said upper surface of said material distribution shell and for carrying it for discharge into said dispensing well.

11. A dental amalgam dispenser according to claim 10 further comprising adjustable metering means for altering the volume of said measuring chamber.

12. A dental amalgam dispenser according to claim 10 further comprising spring biasing means for biasing said transport carriage along said groove to bring said measuring chamber into communication with said channel to said transfer inlet.

13. A dental amalgam dispenser according to claim 12 further characterized in that an arcuate cavity is defined in said flat upper surface of said material distribution shell, and said spring biasing means is a coil spring positioned in said arcuate cavity, and further comprising a handle extending from said shell and a trigger rotatably mounted on said shell and coupled to said carriage, and said trigger has a finger that depends into said arcuate cavity in said shell whereby said coil spring is maintained in compression in said cavity to bear against said finger to thereby bias said trigger and said handle apart.

14. A dental amalgam dispenser according to claim 10 further comprising a micropore filter and a relief vent defined in structure located in juxtaposition relative to said groove and said relief vent leads to said micropore filter and resides in sliding, sealed communication with said measuring chamber when said measuring chamber is in communication with said transfer inlet.

15. A dental amalgam dispenser according to claim 10 further comprising a vacuum break vent defined in structure that is in sliding sealed communication with said measuring chamber when said measuring chamber is in communication with said transfer outlet.

16. A dental amalgam dispenser according to claim 10 further comprising a mounting deck secured to said material distribution shell above said slide means and having a groove with an aperture defined therein above said slide, and a tablet dispensing cartridge with a plurality of parallel, equally spaced vertical tubes of equal diameter for holding columnar stacks of tablets of silver is disposed in said groove, whereby said cartridge is movable along said groove to align a selected one of said tubes with said aperture to dispense tablets from said selected tube through said aperture into said slide.

17. A dental amalgam dispenser according to claim 16 further characterized in that said track includes a positioning lug to ensure alignment of said selected tube with said aperture.

18. A dental amalgam dispenser according to claim 17 further characterized in that said positioning lug fits into said tubes and is configured to project upwardly from said track and to slope upwardly therefrom.

19. A dental amalgam dispenser according to claim 18 further comprising a retaining bracket secured relative to said material distribution shell above said mounting deck and having an elongated opening therein to receive said dispensing cartridge which moves reciprocally therewithin.

* * * * *